(12) United States Patent
Basu et al.

(10) Patent No.: US 8,784,894 B2
(45) Date of Patent: Jul. 22, 2014

(54) METHODS AND DEVICES FOR FORMING TREATMENT AGENT CARRIERS

(75) Inventors: Shubhayu Basu, Mountain View, CA (US); Eugene T. Michal, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1505 days.

(21) Appl. No.: 11/485,934

(22) Filed: Jul. 12, 2006

(65) Prior Publication Data

US 2008/0014276 A1 Jan. 17, 2008

(51) Int. Cl.
*A61K 38/18* (2006.01)
*A61K 9/14* (2006.01)

(52) U.S. Cl.
USPC .................. 424/489; 977/906; 264/5; 514/2

(58) Field of Classification Search
CPC ................................ A61K 38/18; A61K 9/14
USPC ............. 428/402–402.24; 427/213.3–213.26; 264/4–4.7
See application file for complete search history.

(56) References Cited

U.S. PATENT DOCUMENTS

| | | | | |
|---|---|---|---|---|
| 4,343,433 | A | * | 8/1982 | Sickles .............................. 239/3 |
| 4,956,128 | A | * | 9/1990 | Hommel et al. ................... 264/4 |
| 4,981,625 | A | * | 1/1991 | Rhim et al. ...................... 264/13 |
| 6,179,871 | B1 | * | 1/2001 | Halpern ...................... 623/11.11 |
| 2004/0021017 | A1 | | 2/2004 | Sumiyoshi et al. |
| 2004/0058887 | A1 | | 3/2004 | Bowlin et al. |
| 2004/0087464 | A1 | * | 5/2004 | Stoessel et al. ............... 510/407 |

FOREIGN PATENT DOCUMENTS

| | | |
|---|---|---|
| WO | WO 97/49484 | 12/1997 |
| WO | WO 98/56894 | 12/1998 |
| WO | WO 02/076424 | 10/2002 |

OTHER PUBLICATIONS

Michal, Gene, et al., "Methods and Compositions for Treating Post-Myocardial Infarction Damage," U.S. Appl. No. 11/447,340, filed Jun. 5, 2006.
Rietveld, I.B., et al., "Production of Polymer Films with Electrospray", Sep. 13-16, 2005, Proceeding of the 8th Polymers for Advanced Technologies International Symposium, Budapest, Hungary.
"What is Electrospray?", New Objective, Inc., 2004, at <http://www.newobjective.com/electrospray>.
Abbott Cardiovascular Systems Inc., "PCT Search Report and Written Opinion," dated Mar. 4, 2008, PCT/US2007/013315.
Kim, et al., "Production of microsized PMMA droplets using electrospaying with various auxiliary fields," Journal of Cooloid and Interface Science, vol. 299, No. 2, Mar. 2006, pp. 593-598.
Abbott Cardiovascular Systems, IPRP mailed Jan. 22, 2009 for PCT/US2007/013315, 7 pgs.

* cited by examiner

*Primary Examiner* — Randy Gulakowski
*Assistant Examiner* — Jeffrey Washville
(74) *Attorney, Agent, or Firm* — Randy Shen, Esq.; Blakely Sokoloff Taylor & Zafman LLP

(57) ABSTRACT

A method is described including passing a solution having a biodegradable polymer, a solvent and a treatment agent through an electrocharged nozzle to form particles encapsulating the treatment agent. The particles emitted from the electrocharged nozzle may be exposed to a charge opposite that of the nozzle. The particles may be deposited in a collection assembly comprising a liquid phase. A further method including combining a biodegradable polymer, a solvent and a treatment agent to form a solution, electrodepositing the solution in a particle form wherein the particles encapsulate the treatment agent in a collection assembly comprising a liquid phase and mixing the particles with a bioerodable material capable of forming a gel is described. An apparatus having an electrocharged nozzle, a grounded electrode having an opposite charge to that of the nozzle and a collection assembly comprising a liquid phase is further disclosed.

11 Claims, 3 Drawing Sheets

METHODS AND DEVICES FOR FORMING TREATMENT AGENT CARRIERS

FIELD

Methods and devices for encapsulating a treatment agent.

BACKGROUND

Electrospraying is a deposition process in which a substance to be electrosprayed is passed through a charged syringe to form a very fine liquid aerosol or droplets. Electrospray techniques are generally used in the application of paints to metal surfaces. In particular, the fine spray is directed toward the metal surface and is attracted to the metal such that a smooth film of evenly distributed paint or coating is formed.

Recently, electrospraying has further been incorporated into drug delivery techniques. In this aspect, a drug may be combined with a solution prior to or after the solution is passed through a charged syringe. The electrosprayed solution including the drug may then be deposited in a specific shape for subsequent use in vivo. For example, the electrosprayed solution may be deposited in the shape of a skin patch or a dental prosthesis. The patch, for example, may then be placed upon a desired treatment site. In other cases, the electrosprayed solution may be sprayed directly on a treatment site, such as for example a surgical site. Thus, in the above described techniques, the electrosprayed solution is deposited specifically for a predetermined use and may not be collected and applied to other uses. In this aspect, a suitable substrate or body region for the desired use must be identified prior to depositing the material. In this aspect, uses of the electrodeposited materials are limited.

SUMMARY

Methods and devices for electrodepositing particles which may be collected and used for any number of applications are disclosed. The particles may be electrodeposited into a solution (e.g. into a collection vessel including a liquid phase). In one embodiment, the method includes passing a solution comprising a biodegradable polymer, a solvent and a treatment agent through an electrocharged nozzle to form particles encapsulating the treatment agent. Optionally, one or more excipients to stabilize the treatment agent in the solution may be included. In one aspect, suitable treatment agents may include agents that promote angiogenesis (angiogenesis promoting factors), agents that promote cell survival (cell survival promoting factors), and agents that recruit endogenous progenitor and/or stem cells (endogenous recruiting factors) for treatment of post-myocardial infarction. The method further includes exposing the particles emitted from the electrocharged nozzle to a charge opposite that of the nozzle to draw the particles from the nozzle and into a collection assembly comprising a liquid phase. The liquid phase may be any polar solvent. Representatively, the polar solvent may include but is not limited to water or an aqueous buffer. The particles dispersed throughout the liquid phase may be collected by, for example, removing the liquid phase containing the particles from the collection assembly and centrifuging or filtering out the particles or freeze drying the liquid phase.

In another embodiment, a method includes combining a biodegradable polymer, a solvent and a treatment agent through an electrocharged nozzle to form particles encapsulating the treatment agent. Optionally, one or more excipients to stabilize the treatment agent in the solution may be included. The solution may be electrodeposited in a particle form wherein the particle encapsulates the treatment agent in a collection assembly comprising a liquid phase. The method further includes mixing the particles with a bioerodable material capable of forming a gel. The bioerodable material may include a combination of a first component and optionally a second component and one of the first component and the second component may include the particles. Representatively, the bioerodable material may be a two-component gel such as an alginate construct which has alginate, or collagen grafted alginate as a first component and Calcium chloride as a second component; or fibrin glue which comprises mainly fibrinogen as a first component and thrombin as a second component. The gel may serve, in one aspect, to retain the treatment agent at a treatment site within a mammalian tissue for a prolonged period of time so as to beneficially stimulate the effect of the treatment agent. Suitable treatment sites representatively include, but are not limited to, in or around a blood vessel such as a coronary blood vessel, thoroscopic surgery sites, orthoscopic surgery sites, and laparoscopic surgery sites.

In yet another embodiment, an apparatus is disclosed including an electrocharged nozzle through which a solution including a biodegradable polymer, solvent and a treatment agent through an electrocharged nozzle to form particles encapsulating the treatment agent. Optionally, one or more excipients to stabilize the treatment agent in the solution may be included. The apparatus further includes a grounded electrode having an opposite charge to that of the nozzle to attract the solution from the nozzle toward a collection assembly comprising a liquid phase positioned proximal to the grounded electrode.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION

Figure 1:
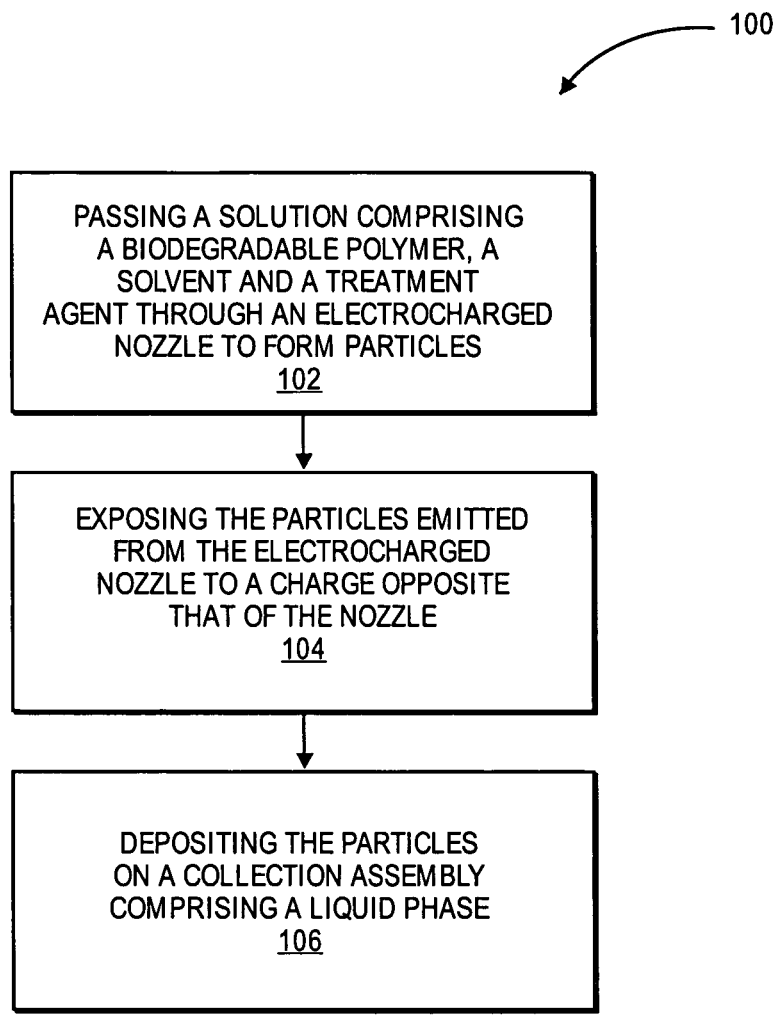
FIG. 1 shows a flowchart of a method for encapsulating a treatment agent within a carrier.
Figure 2:
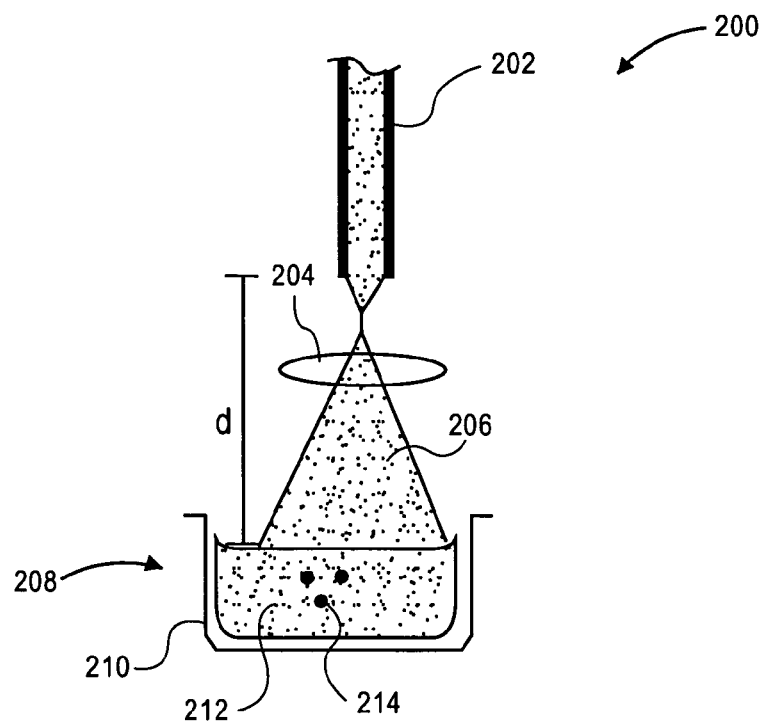
FIG. 2 shows a schematic side view of a first embodiment of an electrospray apparatus.

Methods and devices described herein provide for electrodeposited particles which may be collected and used for any number of applications. The particles may be electrodeposited into a solution (e.g. into a collection vessel including a liquid phase). In particular, a method of forming and collecting electrodeposited particles having a treatment agent encapsulated therein is disclosed. The particles may be collected and delivered to a treatment site in any form deemed desirable. For example, in one context, the particles may be collected and suspended in a bioerodable material for delivery to a desired treatment region. In some embodiments, the bioerodable material may be a one-component or a two-component gel similar to that which is described in commonly owned co-pending U.S. patent application Ser. No. 11/447,340, titled Method and Composition for Treating Post-Myocardial Infarction Damage of Michal et. al. filed on Jun. 5, 2006 and incorporated herein by reference. The bioerodable material may include a combination of a first component and a second component and one or both of the first component and the second component may include the particles. Representatively, the bioerodable material may be an alginate-collagen combination or a fibrin glue combination suitable for delivery to a desired treatment site within a mammalian host. Representatively, the bioerodable material may be a two-component gel such as an alginate construct which has alginate or collagen grafted alginate as a first component and Calcium chloride as a second component; or fibrin glue which comprises mainly fibrinogen as a first component and thrombin as a second component. In other embodiments, the collected particles may be suspended in a liquid substance, such as a saline solution, plasma, serum or any other physiological buffer, for intravenous delivery to the desired treatment site or combined with a topical composition for topical delivery to the desired treatment site.

In this aspect, the electrodeposited particles with a treatment agent therein may be used as carriers to facilitate delivery of a treatment agent according to a variety of methods to any number of tissue regions. A suitable carrier (hereinafter interchangeably referred to as "particle") may take the form of a nanoparticle (e.g., nanosphere), microparticle (e.g., microsphere), liposome, and the like particles, as the situation may dictate. As used herein, treatment agents are intended to include, but are not intended to be limited to, drugs, biologically active agents, chemically active agents, therapeutic agents, and the like, and pharmaceutical compositions thereof, which can be used to deliver a treatment agent to a treatment site as described herein.

In one aspect, the carrier may be used to encapsulate a treatment agent in the form of, for example, a growth factor (e.g. insulin-like growth factor 1), small peptide and/or drug which may facilitate tissue repair when delivered to a desired treatment site. The encapsulated treatment agent may further include agents that promote angiogenesis (angiogenesis promoting factors), agents that promote cell survival (cell survival promoting factors), and agents that recruit endogenous progenitor and/or stem cells (endogenous recruiting factors) for treatment of post-myocardial infarction.

In one aspect, the carrier loaded with the treatment agent may be delivered during a surgical procedure such as an open heart surgery (e.g., Cabbage Coronary Bypass Graft (CABG)) procedure in which areas of the heart may be treated with, for example, growth factors encapsulated within the carrier, for affecting therapeutic angiogenesis. Still further the carrier loaded with the treatment agent may be used to facilitate delivery of a treatment agent to a desired treatment region during surgical procedures such as cancer-related procedures (e.g., brain, abdomen, or colon cancer procedures or surgeries) or endoscopic procedures such as orthoscopic surgery for joints (e.g., knee), laparoscopic surgery for the abdomen, and thoroscopic procedures related to chest injuries or treatments.

The carrier loaded with the treatment agent may be formed from a solution including a biodegradable polymer, a solvent and a treatment agent through an electrocharged nozzle to form particles encapsulating the treatment agent. Optionally, one or more excipients to stabilize the treatment agent in the solution may be included. The biodegradable polymer may be a sustained-release polymer such that the formed carrier is a sustained-release carrier which releases the treatment agent over a period of time. Examples of sustained-release biodegradable polymers which may be used include, but are not limited to, poly (L-lactide), poly (D,L-lactide), poly (glycolide), poly (lactide-co-glycolide), polycaprolactone, polyanhydride, polydiaxanone, polyorthoester, polyamino acids, or poly (trimethylene carbonate) and combinations thereof. Still further, a suitable biodegradable polymer may include, but is not limited to, a native collagen such as type I collagen.

The solvent may be any solvent capable of dissolving the polymer. Representatively, the solvent may be an organic solvent such as, but not limited to, hexafluoroisopropanol (HFIP).

The excipient may be any excipient capable of stabilizing the treatment agent (e.g., a protein) within the solution. Representatively, the excipient may be a buffer or stabilizer such as, but not limited to, a surfactant, for example, tween 20, tween 80 and/or human serum albumin. Alternatively, the excipient may be a sugar such as, but not limited to, sorbitol, mannitol, glycerol, lactose, trehalose, sucrose and/or glucose. Still further, the excipient may be an amino acid such as, but not limited to, glycine, arginine and/or glutamic acid. In some embodiments, the excipient may be an antioxidant, including, but not limited to, ascorbic acid. In other embodiments, the excipient may be a hydrophilic polymer such as, but not limited to, poly(ethylene glycol) (PEG), polyvinylpyrrolidone (PVP), and cellulose esters.

The treatment agent-infused polymer solution as described above may then be subjected to an electrospray technique as will be described more fully below. As the solvent evaporates during processing, the treatment agent incorporates and distributes within the polymer by non-covalent interactions.

In one embodiment, the electrospray technique may include an electrospray apparatus having an electrocharged nozzle, a grounded electrode and a collection assembly including a liquid phase. The dimensions of the nozzle may be selected based upon factors such as characteristics of a solution to be passed through the needle, desired flow rate and desired voltage potential. Representatively, the electrocharged nozzle may be a stainless steel capillary or needle having an outer diameter of about 0.36 millimeters (mm) and an inner diameter of about 0.1 mm. There are various ways to charge the nozzle. For example, a charge source may be connected to the nozzle or in other cases an electrode may be added in the middle of a tube carrying the solution to the needle. The electrocharged nozzle may have a positive or a negative charge at a sufficient voltage to electrically charge a liquid passing through the nozzle. Representatively, a suitable voltage applied to the nozzle may be from about one kilovolt (kV) to about 20 kV. Eventually the liquid reaches a point where it can hold no more charge (i.e. critical point) and separates into a plume of highly charged particles.

In addition to facilitating separation of the liquid, the applied voltage affects the size of the charged particles formed from the solution. In particular, increasing the applied voltage to the solution flowing through the nozzle widens the plume of charged particles released at the end of the nozzle. The particles are thus more spread out allowing for greater solvent evaporation and in turn decreased particle size. Accordingly, where a smaller particle size is desired, a higher voltage (e.g., closer to about 20 kV) may be applied. Alternatively, where a larger particle size is desired, a lower voltage (e.g., closer to about one kV) may be applied.

The grounded electrode may be positioned between the electrocharged nozzle and the collection assembly provided it is in the shape of a ring or any other geometry which allows passage of the electrosprayed particles to the collection assembly. In this aspect, the particles emitted from the nozzle are exposed to a charge from the grounded electrode. It should be recognized, however, that the particles maintain the same charge as the nozzle. The grounded electrode may be positioned proximal to the collection assembly and should have an opposite charge to that of the nozzle such that it attracts charged particles from the nozzle and in the direction of the collection assembly. In one embodiment, the grounded electrode may be any material capable of holding an electrical charge. In one aspect, the grounded electrode may be a metal or metal alloy including, but not limited to, a copper, silver, aluminum, gold or steel. The grounded electrode may be of any dimension suitable for allowing the particulate solution released from the electrocharged nozzle to pass through. In other embodiments, the grounded electrode may be of any dimension suitable for positioning the grounded electrode on or within the collection assembly.

Figure 3:
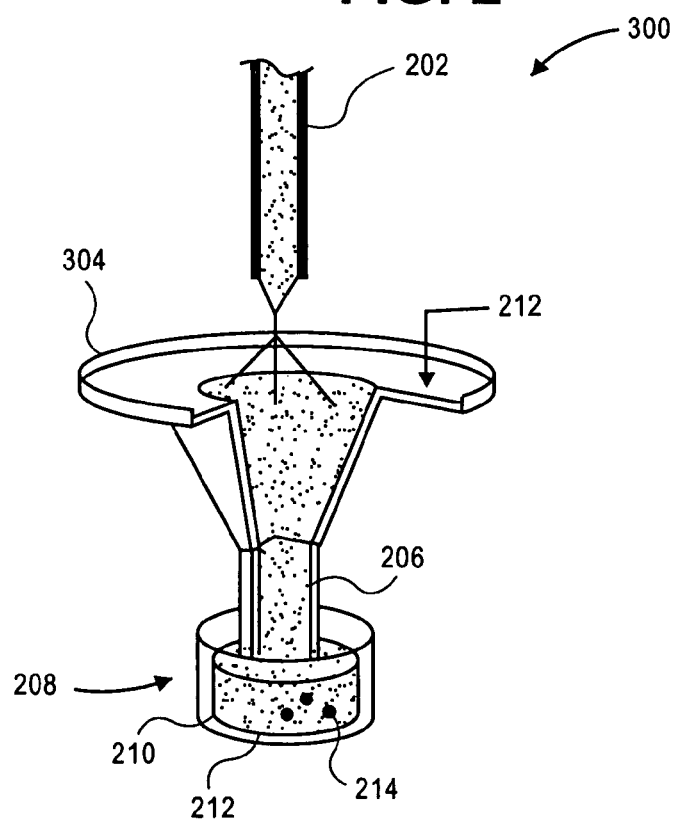
FIG. 3 shows a cross section of a second embodiment of an electrospray apparatus.

In one embodiment, the collection assembly may be any collection mechanism capable of accepting the electrocharged particles deposited thereon and allowing for removal of the particles. In one aspect, the collection assembly may include a collection vessel including, but not limited to, a container, a basin, a dish, a receptacle or a beaker. In other embodiments, the collection assembly may be a flat surface with a nonstick feature, such as, for example, a disc shaped object having a Teflon® coating. The collection assembly may have any suitable dimension as the situation may dictate.

In one embodiment, a liquid phase may be retained within the collection vessel such that the electrocharged particles may be suspended in the liquid phase and collected therefrom. The liquid phase may be any liquid in which the polymer is insoluble. Representatively, the liquid phase may include any polar solvent, including but not limited to, water, or any other aqueous buffer solutions.

In one aspect, a method is described for forming a treatment agent carrier. Representatively, FIG. 1 shows a flowchart of a method for encapsulating a treatment agent within a carrier. In one embodiment, a solution comprising a biodegradable polymer, a solvent and a treatment agent may be passed through an electrocharged nozzle (block 102). Optionally, the solution may include one or more excipients to stabilize the treatment agent in the solution. The treatment agent may be any treatment agent found desirable for the particular condition to be treated. Representatively, where a cardiovascular condition is to be treated, the treatment agent may be an angiogenesis promoting factor, a cell survival promoting factor, and/or an endogenous recruiting factor such as an agent that recruit endogenous progenitors and/or stem cells.

The amount of polymer, solvent and treatment agent in the solution may be that which is found suitable for forming micro and/or nano sized particles capable of encapsulating the treatment agent. The relative ratio of each component may be tailored to specific applications. In one aspect, the concentration of polymer within the initial solution may be tailored to accommodate a desired particle size. The concentration of polymer within the initial solution controls the surface tension of the solution which in turn affects the ability of the solution to separate into droplets upon release from the electrocharged nozzle. If the polymer concentration and in turn the surface tension is too high, as is the case in electrospinning, the solution will not separate into particles but instead fibers upon release from the electrocharged nozzle. In this aspect, a concentration of polymer within the solution suitable for forming particles may be between about 0.005 weight percent (wt %) and about 0.5 wt %. Where a smaller particle size is desired, for example less than 10 micrometers, a polymer concentration within the solution closer to 0.005 wt % than 0.5 wt % may be used. Alternatively, where a larger particle size is desired, for example greater than 10 micrometers, a higher concentration of the polymer in solution, for example closer to 0.5 wt % may be used.

A plume of particles emitted from the nozzle may be exposed to a charge opposite that of the nozzle (block 104). In this aspect, the opposite charge may attract the particles to the collection assembly as previously described while the charge of the particles remains the same. The particles may then be deposited in the collection assembly comprising the liquid phase (block 106). Once the particles are deposited, they may be collected from the liquid phase of the collection assembly by removing the liquid phase with the particles suspended therein from the collection assembly and separating out the particles. In one aspect, the particles may be separated from the liquid phase by any standard technique capable of separating out the particles without disrupting or otherwise destroying the particle structure. Standard techniques may include, but are not limited to, sedimentation, centrifugation, filtration or freeze drying. The collected particles may then be combined with any substance suitable for facilitating delivery of the treatment agent to a treatment site, for example a gel forming component or a buffer. In other aspects, the particles alone may be delivered to a treatment site.

Referring now to FIGS. 2 to 5, embodiments of the above described electrospray assembly are described in more detail. FIG. 2 shows a schematic side view of a first embodiment of an electrospraying assembly. In this aspect, electrospray assembly 200 includes an electrocharged nozzle 202, a grounded electrode 204 and a collection assembly 208. Grounded electrode 204 is positioned between electrocharged nozzle 202 and collection assembly 208. Electrocharged nozzle 202 may have a positive charge and grounded electrode 204 may have a negative charge such that a plume of particles 206 (e.g. particles encapsulating a treatment agent) released from electrocharged nozzle 202 are drawn toward collection assembly 208. In this aspect, grounded electrode 204 is in the shape of a ring such that the particles pass through the ring and into collection assembly 208. Electrocharged nozzle 202 and the liquid level in collection assembly 208 may be a sufficient distance, d, from one another such that the solvent within the solution may evaporate while traveling from electrocharged nozzle 202 to collection assembly 208. In one aspect, d may be between about five centimeters (cm) and about 25 cm, in other aspects, d may be between about 10 cm and about 20 cm. It is further recognized that evaporation of the solvent modifies the particle size, thus where d is on the order of 20 cm, the particle size may be smaller than where d is on the order of 5 cm. In this aspect, d may be adjusted depending upon the desired particle size.

In this embodiment, collection assembly 208 may include a collection vessel 210 and a liquid phase 212 retained within collection vessel 210. As illustrated in FIG. 2 by enlarged particles 214, particles from plume 206 are deposited in collection assembly 208 and become suspended in liquid phase 212 for subsequent collection.

FIG. 3 shows a cross section of a second embodiment of an electrospraying apparatus. In this aspect, electrospray assembly 300 includes an electrocharged nozzle 202, a grounded electrode 304 and a collection assembly 203. Grounded electrode 304 is positioned between electrocharged nozzle 202 and collection assembly 208. Electrocharged nozzle 202 may have a positive charge and grounded electrode 304 may have a negative charge such that a plume of particles 206 (e.g. particles encapsulating a treatment agent) released from electrocharged nozzle 202 is drawn toward collection assembly 208. In this aspect, grounded electrode 304 is in the shape of a funnel with a continuous falling thin film of liquid phase 212 over it. The falling thin film of liquid will prevent coating of the grounded electrode with electrosprayed particles and will wash the particles down into collection vessel 210 positioned below. Electrocharged nozzle 202 and grounded electrode 304 may be a sufficient distance from one another such that the solvent within the solution may evaporate while traveling from electrocharged nozzle 202 to liquid phase 212 of collection assembly 208. In one aspect, the solution may travel a distance of between about 5 cm and about 25 cm, in other aspects, the distance may be between about 10 cm and about 20 cm. As illustrated in FIG. 3 by enlarged particles 214, particles from plume 206 are deposited in collection assembly 208 are suspended in liquid phase 212 for subsequent collection.

Figure 4:
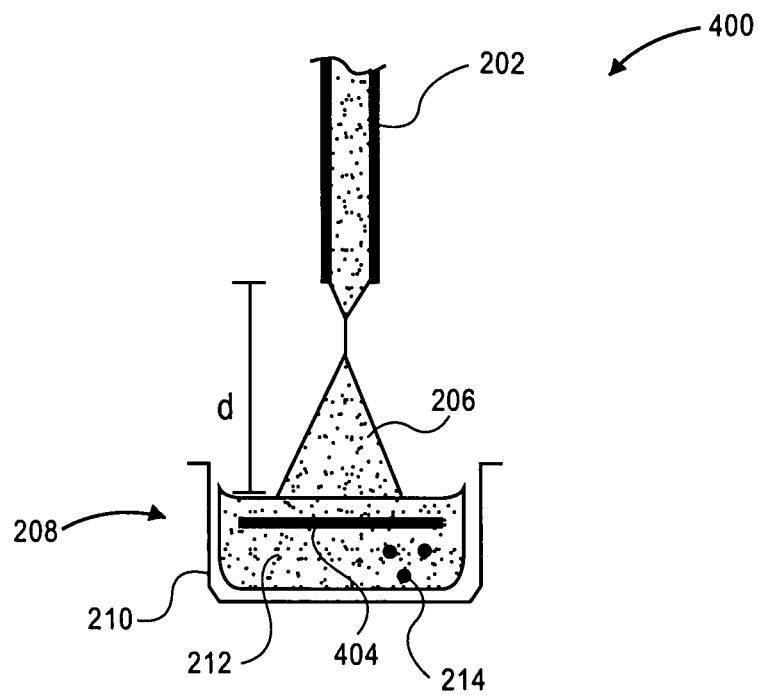
FIG. 4 shows a schematic side view of a third embodiment of an electrospray apparatus.

FIG. 4 shows a schematic side view of a third embodiment of an electrospraying apparatus. In this aspect, electrospray assembly 400 includes an electrocharged nozzle 202, a grounded electrode 404 and a collection assembly 203. Grounded electrode 404 is positioned within liquid phase 212 retained in collection vessel 210 of collection assembly 208. Electrocharged nozzle 202 may have a positive charge and grounded electrode 404 may have a negative charge such that a plume of fluid 206 (e.g. particles encapsulating a treatment agent) released from electrocharged nozzle 202 is drawn toward collection assembly 208. Grounded electrode 404 may be in the shape of a ring, disc or any similar planar object capable of being retained within liquid phase 212 of collection vessel 210. In this aspect, particles dispersed from the solution are deposited into collection assembly 208. Electrocharged nozzle 202 and the level of fluid in the collection assembly 208 may be a sufficient distance, d, from one another such that the solvent within the solution may evaporate while traveling from electrocharged nozzle 202 to collection assembly 208. In one aspect, d may be between about 5 cm and about 25 cm, in other aspects, d may be between about 10 cm and about 20 cm. As illustrated in FIG. 4 by enlarged particles 214, particles from plume 206 are deposited in collection assembly 208 and are suspended in liquid phase 212 for subsequent collection.

Figure 5:
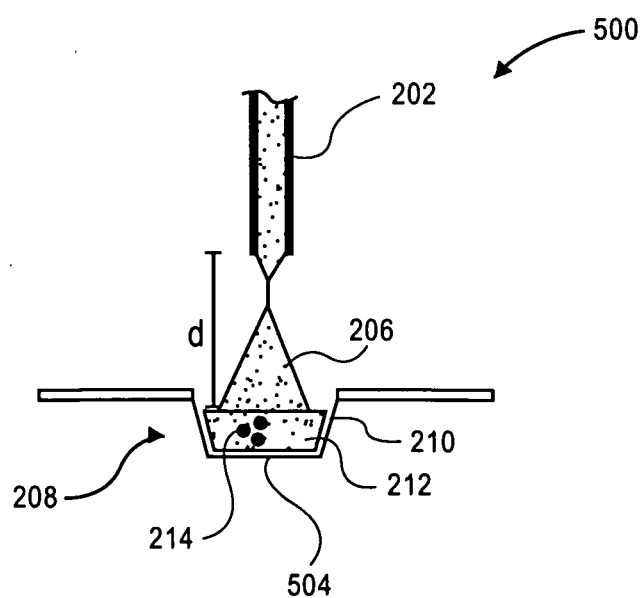
FIG. 5 shows a schematic side view of a fourth embodiment of an electrospray apparatus.

FIG. 5 shows a schematic side view of a fourth embodiment of an electrospraying apparatus. In this aspect, electrospray assembly 500 includes an electrocharged nozzle 202, a grounded electrode 504 and a collection assembly 203. Grounded electrode 504 forms a bottom surface of collection vessel 210 of collection assembly 208. In this aspect, liquid phase 212 retained in collection vessel 210 is positioned between electrocharged nozzle 202 and grounded electrode 504. Electrocharged nozzle 202 may have a positive charge and grounded electrode 504 may have a negative charge such that a plume of fluid 206 (e.g. particles encapsulating a treatment agent) released from electrocharged nozzle 202 is drawn toward collection assembly 208. In this aspect, particles dispersed from the solution are deposited into collection assembly 208. Electrocharged nozzle 202 and the level of liquid in the collection assembly 208 may be a sufficient distance, d, from one another such that the solvent within the solution may evaporate while traveling from electrocharged nozzle 202 to collection assembly 208. In one aspect, d may be between about 5 cm and about 25 cm, in other aspects, d may be between about 10 cm and about 20 cm. As illustrated in FIG. 5 by enlarged particles 214, particles from plume 206 are deposited in collection assembly 208 and are suspended in liquid phase 212 for subsequent collection.

In the preceding detailed description, specific embodiments are presented. Those embodiments include apparati (devices) and methods for encapsulating a treatment agent suitable for delivery to a treatment site. Cardiovascular treatment therapies in particular are highlighted. It will, however, be evident that various modifications and changes may be made thereto without departing from the broader spirit and scope of the claims. For example, contemplated treatment therapies include therapies, in addition to cardiovascular treatment therapies, where blood vessels or tissues are identified for localized treatment agents in the context of surgery or other medical procedure. The specification and drawings are, accordingly, to be regarded in an illustrative rather than a restrictive sense.

What is claimed is:

1. A method comprising:
    passing a solution comprising a biodegradable polymer, a solvent and a treatment agent through an electrocharged nozzle to form charged particles encapsulating the treatment agent;
    exposing the charged particles emitted from the electrocharged nozzle to a grounded electrode having a charge opposite that of the nozzle, wherein the grounded electrode is positioned a distance from the electrocharged nozzle sufficient to draw the charged particles toward a collection assembly and allow for solidification of the charged particles through solvent evaporation from the charged particles while the charged particles are traveling to the collection assembly; and
    depositing the charged particles in the collection assembly, wherein the collection assembly comprises a liquid phase, the liquid phase comprising a polar solvent and the grounded electrode is positioned within the liquid phase,
    wherein the biodegradable polymer is insoluble in the liquid phase.

2. The method of claim 1, wherein the grounded electrode is positioned between the nozzle and the collection assembly.

3. The method of claim 1, wherein the collection assembly comprises a collection vessel having the liquid phase disposed therein.

4. The method of claim 1, wherein the charged particles are one of a microsphere or a nanosphere.

5. The method of claim 1, wherein the treatment agent is selected from the group consisting of angiogenesis promoting factors, cell survival promoting factors and endogenous recruiting factors.

6. The method of claim 1, wherein the grounded electrode is one of a ring, a cylinder or a disc.

7. The method of claim 1, wherein the liquid phase comprises a liquid in which the polymer is insoluble.

8. The method of claim 1, further comprising separating charged particles suspended in the liquid phase of the collection assembly by at least one of sedimentation, centrifugation, filtration or freeze drying.

9. The method of claim 1, wherein the solution further comprises an excipient.

10. The method of claim 1 further comprising:
    controlling a size of the charged particles by modifying a voltage applied to the electrocharged nozzle.

11. The method of claim 1 further comprising:
    controlling a size of the charged particles by modifying the distance between the electrocharged nozzle and the grounded electrode.

* * * * *